United States Patent [19]

Amphlett et al.

[11] Patent Number: 4,508,709

[45] Date of Patent: Apr. 2, 1985

[54] PROCESS FOR PURIFYING FACTOR VIII:C

[75] Inventors: Godfrey W. Amphlett, Mount Vernon, N.Y.; Michael E. Hrinda, Wilton, Conn.

[73] Assignee: Armour Pharmaceutical Company, Tarrytown, N.Y.

[21] Appl. No.: 557,805

[22] Filed: Dec. 5, 1983

[51] Int. Cl.³ .............................................. A61K 35/16
[52] U.S. Cl. ..................................................... 424/101
[58] Field of Search ........................................ 424/101

[56] References Cited

U.S. PATENT DOCUMENTS 4,361,509  11/1982  Zimmerman et al. ............... 424/101

OTHER PUBLICATIONS

Austen, D. E. G., "The Chromatographic Separation of Factor VIII on Aminohexyl Sepharose", British Journal of Hematology, 1979 (43), pp. 669–674.

Morgenthaler, J. J., "Chromatography of Antihemophilic Factor on Diaminoalkane-and Aminoalkane-Derivatized Sepharose", Thromb. Haemostas., 1982, 47(2), pp. 124–127.

Faure, A., et al., "Note, Improved buffer for the chromatographic separation of Factor VIII coagulant", J. Chromatography, 1983 (257), pp. 387–391.

Austen, D. E. G., et al., "Factor VIII Fractionation on Aminohexyl Sepharose with Possible Reduction in Hepatitis B Antigen", Thromb. Haemostas., (1982) 48(1), pp. 46–48.

*Primary Examiner*—Sam Rosen

[57] ABSTRACT

Factor VIII:C is purified by chromatographic absorption on aminohexyl agarose at a pH above 5.5 up to about 8, and preferably 6.5 to 7.2, and a conductivity of about 25 to about 35 mS/cm.

21 Claims, No Drawings

PROCESS FOR PURIFYING FACTOR VIII:C

BACKGROUND OF THE INVENTION

1. Field of the Invention

The present invention relates to the purification of the procoagulant Factor VIII:C from source material such as plasma or cryoprecipitate which contains antihemophilic factor (herein, "AHF").

It is generally believed in this field that AHF in its natural form as obtained from plasma consists of aggregates of two molecular entities, which are termed Factor VIII:R and Factor VIII:C. Factor VIII:C is biologically active in correcting the coagulation defect of Hemophilia A. Factor VIII:R, also known as Factor VIII:WF (von Willebrand Factor), is biologically active in correcting the coagulation defect of von Willebrand's disease, a disorder of platelet aggregation. It is highly desirable to be able to purify Factor VIII:C with respect to Factor VIII:R and the other plasma proteins with which Factor VIII:C is normally found, including in particular fibronectin and fibrinogen.

2. Description of the Prior Art

Previously known processes for purifying Factor VIII:C introduce losses of yield and/or purity which up to now have been tolerated. The present invention achieves higher levels of purification and yield, without deactivation, in a manner which is not suggested by the prior art.

D. E. G. Austen, "The Chromatographic Separation of Factor VIII on Aminohexyl Sepharose", in British Journal of Hematology, 1979, (43) 669–674, described a chromatographic separation process in which human or porcine Factor VIII concentrate was passed through a column of 6-amino-n-hexyl-substituted agarose. The column and all eluting solutions were at a pH of 5.5. A high degree of separation of Factor VIII:C from Factor VIII:R, and a high degree of purification of Factor VIII:C from other proteins, were obtained. However, the total recovery of human Factor VIII:C was only 35–40%, and for porcine Factor VIII:C was only 24–30%. The authors indicate that more acidic pH values in the buffers (down to a pH of about 5.2) favor higher purification of Factor VIII, and they purposely chose the pH of 5.5 in order to have as acidic an environment as possible without suffering too low a yield. Thus, the authors teach away from higher (that is, less acidic) pH values.

Several more recent publications have continued to insist on maintaining an acid pH in the chromatographic column. Morgenthaler, "Chromatography of Antihemophilic Factor on Diaminoalkane- and Aminoalkane-Derivatized Sepharose", Thromb. Haemostas. 47(2) 124–127 (1982), found that when AHF was chromatographed on Sepharose CL-2B agarose gel at pH values of 6.0, 6.5 and 7.0, no significant separation of Factors VIII:C and VIII:R could be obtained. Chromatography of AHF at a pH of 5.5 produced a very marked separation between Factors VIII:C and VIII:R. An even more recent paper, by Faure et al., Note, "Improved buffer for the chromatographic separation of Factor VIII coagulant," J. Chromatography 257 (1983), 387–391, retains the pH value of 5.5 indicated by Austen and attempts to improve the performance of that chromatographic procedure by adding compounds to the buffers. And Austen, in an attempt to improve the results obtained in his article discussed above, continues to operate at a pH of 5.5 and achieves a yield of Factor VIII:C of about 40%, in Austen et al., "Factor VIII Fractionation on Aminohexyl Sepharose with Possible Reduction in Hepatitis B Antigen", Thromb. Haemostasis, 48(1), 46–48 (1982).

To our knowledge, Factor VIII:C has been applied to a column at a pH closer to neutral only in the instance in which Factor VIII:R and a large number of other contaminants, including fibronectin and fibrinogen, have already been separated from the Factor VIII:C. Specifically, in U.S. Pat. No. 4,361,509, Zimmerman et al. employ a column bearing monoclonal antibodies to Factor VIII:R to recover a dilute solution of Factor VIII:C that has been ultrapurified of Factor VIII:R. The solution of ultrapurified Factor VIII:C is concentrated by adjusting the pH to 6.8 with buffer, applying the solution to a column of aminohexyl agarose, and then eluting the Factor VIII:C from the column. This concentration step starts from material which is about 1000 times as pure as the starting material, and thus does not suggest what the results would be if substantial amounts of VIII:R were present; indeed, if one who had read this patent were presented with source material containing both Factors VIII:C and VIII:R one would employ the extremely effective monoclonal antibody-column separatory technique to remove the Factor VIII:R. Thus, the teaching of the U.S. Pat. No. 4,361,509 patent regarding the conditions for employing the aminohexyl agarose column does not contradict or modify the teachings of the articles discussed above.

SUMMARY OF THE INVENTION

The process of the present invention achieves the advantageous combination of yield and purification under conditions that are wholly unexpected, and indeed disfavored, by the prior art.

Specifically, the invention is a process for purifying Factor VIII:C in high yield from source material containing Factor VIII:C and VIII:R, comprising (a) providing an aqueous solution of said source material which has a pH above 5.5 to about 8.0 and a conductivity of about 25 mS/cm to 35 mS/cm, (b) adsorbing Factor VIII:C and Factor VIII:R from said solution onto aminohexyl agarose, (c) eluting the Factor VIII:R from the aminohexyl agarose, and then (d) eluting the Factor VIII:C from the aminohexyl agarose, thereby providing a solution of Factor VIII:C which is purified with respect to the source material.

DETAILED DESCRIPTION OF THE INVENTION

Source material suitable for use in this invention includes any material containing Factor VIII:C with one or more other plasma proteins. Particular examples are materials which contain Factor VIII, i.e. the complex of Factors VIII:C and VIII:R, such as plasma, commercial Factor VIII concentrates, and cryoprecipitate obtained from plasma, as well as product fractions and otherwise discarded side fractions from the well-known Cohn fractionation process. Human-source material, as well as bovine and porcine, can be treated. Proteins besides Factor VIII:R that can be present include fibrinogen, fibronectin, and albumin.

When cryoprecipitate is the starting material, it should be reconstituted in an aqueous buffer in the manner known generally to those skilled in this art, but observing the novel pH range and ionic strength which are to be observed in accordance with the present invention. Plasma and plasma concentrates are already in a suitable state for applying to the column except that these too, should have their pH and ionic strength adjusted appropriately by aqueous buffer.

The pH can be adjusted by adding an aqueous solution of compounds which will buffer the pH of the resulting solution to within the desired range of 6.5 to 7.2, and which do not disturb the activity of the Factor VIII:C. Many such solutions are known to the skilled practitioner; one example is a buffer solution containing 20 mM imidazole, 0.1 M lysine, and 0.02% sodium azide (hereinafter, "Buffer A"), which buffers the pH to about 6.8. Another example is 10 mM histidine, 0.1 M lysine, and 0.02 wt. % sodium azide.

The conductivity can be adjusted simply by adding sodium chloride in a sufficient amount so that with the other ions present the overall conductivity lies between about 25 mS/cm and about 35 mS/cm (milli-Siemens per cm, equivalent to $10^{-3}$ mhos/cm). Sodium chloride can be added as a solid or as an aqueous solution, to the buffer solution or directly to the Factor VIII:C source solution. If the conductivity is too high or low, binding capacity is lost, and if it is too low the purity of the product suffers as well.

The adsorbent material employed in the column is aminohexyl agarose. This, as is well known in this art, is agarose having omega-amino side chains. There shoud be sufficient side chains to permit the desired purification to take place. Advantageously, there should be at least about 10 micromoles of aminohexyl side chains per gram of agarose, and more advantageously at least about 15 micromoles/g. Amounts of adsorbent are given in this specification and the claims as the wet weight, defined as the weight of material which has been filtered under suction to the point at which the filter cake cracks. Satisfactory aminohexyl agarose is available commercially under the trade name "Aminohexyl Sepharose", sold by Pharmacia Fine Chemicals Company, having about 12 micromoles of aminohexyl chains per gram of material.

The absorbent is prepared by equilibrating it, i.e. washing it, in a buffer to give it a pH above 5.5 up to about 8.0, preferably 6.0 to 7.5, and more preferably 6.5 to 7.2. The ratio of source material to absorbent should not exceed the capacity of the absorbent resin, which is a value that can readily be determined by those familiar with chromatographic separations. Generally, the capacity is 5–10 VIII:C units per gram of resin when cryoprecipitate is used, and several times higher when more purified source material is used. The absorption can be carried out in a batch mode or in a column, in either case employing techniques and equipment customary in this field for chromatographic separations of this type.

The source material, which has separately already been adjusted to the same pH as the absorbent, is applied to the absorbent allowing a sufficient contact time for the desired protein-absorbent interactions to occur. In the column mode, typical satisfactory flow rates are about 5 column volumes per hour, but not so high that the column is compacted or disrupted. The material that passes through the column first in this step will have been depleted in Factor VIII:C, as well as depleted in Factor VIII:R if the Factor VIII:C in the source material was present complexed with Factor VIII:R. The removal of non-adsorbed material can be assisted by washing the column with buffer solution such as Buffer A containing 0.3 M NaCl.

After the bulk of non-adsorbed material has been washed from the column (as indicated by an absorbance at 280 nm of the eluate of 1 or less), washing is continued using Buffer A containing 0.3 M NaCl and 10 mM $CaCl_2$. $CaCl_2$ is known in the art to stabilize Factor VIII:C, but cannot be used earlier because of the danger of activating clotting factors, leading to fibrin clots on the resin and potential degradation of Factor VIII:C. Washing of the resin is effective in removing fibronectin, fibrinogen and the bulk of contaminating protein.

Where the Factor VIII:C is complexed with Factor VIII:R, it is advantageous to elute the column next with an eluant which is effective to desorb most of the Factor VIII:R remaining on the column which was not eluted by the washing. Some Factor VIII:C may elute as well in this step, but this is compensated for by the fact that the Factor VIII:C which does not elute in this step will be recovered in more highly purified form and with a yield which still surpasses prior art techniques by a substantial factor. The Factor VIII:R can be eluted with an eluant comprising the aforementioned Buffer A containing dissolved therein 0.4 M NaCl and 10 mM $CaCl_2$. The eluted fraction is collected and represents an enriched source of Factor VIII:R. This elution step can be omitted if very high yields of Factor VIII:C are desired (e.g. at least 80% to 90%) and the presence of Factor VIII:R in the eluted Factor VIII:C product can be tolerated.

The Factor VIII:C remaining on the absorbent is next eluted under conditions effective to desorb the Factor VIII:C without decreasing its biological activity. A satisfactory eluant comprises the aforementioned Buffer A containing dissolved therein 0.3 M to 0.5 M $CaCl_2$, preferably 0.5 M $CaCl_2$. Another is Buffer A containing 1 M NaCl. The eluted fraction is collected and can be further processed or used per se as a source of Factor VIII:C for therapeutic purposes.

When plasma is the source material, the process should be carried out with the addition of small but effective amounts of inhibitors of proteolytic degradation, such as benzamidine, pancreatic trypsin inhibitor, or hirudin. No such inhibitors are necessary when the source material is cryoprecipitate or material of higher Factor VIII:C purity.

The invention will be described further in the following Examples.

EXAMPLE 1

This example compares purification of antihemophilic factor from human cryoprecipitate by the claimed process and by related published procedures. All procedures were performed at room temperature.

a. Purification by the claimed process

Human cryoprecipitate (3 g) was resuspended, using a vibromixer, in 10 ml Buffer A (20 mM imidazole, 0.1 M lysine, 0.02% azide, pH 6.8) containing 0.3 M NaCl. Vitamin K dependent proteases were removed by treatment with aluminum hydroxide gel (Rehsorptar ®, Armour Pharmaceutical Co.). The solution was stirred with 1/30 volume Rehsorptar for 10 minutes, centrifuged at 10,000×g for 5 minutes and readsorbed with the same amount of Rehsorptar for 10 minutes. After centrifuging (10,000×g for 5 minutes), the solution was passed through two layers of cheese cloth. The resulting solution had a conductivity of 32 mS/cm. 2.5 ml of this solution was applied to a 10 ml column of AH-Sepharose (Pharmacia) (10×0.55 cm) equilibrated in Buffer A containing 0.3 M NaCl at a flow rate of 12 ml/h. The column was washed with equilibration buffer (Buffer A containing 0.3 M NaCl) until the absorbance at 280 nm of the eluate was less than 0.1. The column was further washed with Buffer A containing 0.3 M NaCl and 10 mM CaCl$_2$, then eluted, first with Buffer A containing 0.4 M NaCl and 10 mM CaCl$_2$, then with Buffer A containing 0.5 M CaCl$_2$.

| Fraction | Factor VIII:C (U/mg) | Factor VIII:C Total Units | Yield % | × Purification |
|---|---|---|---|---|
| Cryoprecipitate Solution | 0.245 | 24.2 | 100 | 1 |
| Unbound | 0 | 0 | 0 | — |
| Buffer A + 0.3M NaCl + 10 mM CaCl$_2$ Wash | 0 | 0 | 0 | — |
| Buffer A + 0.4M NaCl + 10 mM CaCl$_2$ Wash | 1.18 | 4.1 | 17 | 4.8 |
| Buffer A + 0.5M CaCl$_2$ Wash | 8.4 | 17.6 | 73 | 34.3 |

A pool of the two fractions containing significant Factor VIII:C activity would have 90% of the applied Factor VIII:C at a specific activity of 3.9 U/mg for a 16-fold purification.

b. Purification by the method of Austen 2.5 g human cryoprecipitate was resuspended, using a vibromixer, in 715 ml Buffer B (0.1 M lysine, 0.1 M sodium acetate, pH 5.5) and adsorbed twice with Rehsorptar as in (a). The pH of the solution, found to be 6.5 at this point, was lowered to 5.5 by slow addition of 10% acetic acid with good stirring. A heavy, gelatinous precipitate was removed by centrifugation (10,000×g for 20 min) and passage through two layers of cheesecloth. 3.5 ml of clarified cryoprecipitate solution was applied to a 10 ml column of AH-Sepharose (Pharmacia) (10×0.55 cm), equilibrated in Buffer B, at a flow rate of 12 ml/h. The column was washed with Buffer B until the adsorbance at 280 nm of the eluate was less than 0.1, then eluted with Buffer B containing 0.2 M NaCl and finally with Buffer B containing 1 M NaCl.

| Fraction | Factor VIII:C (U/mg) | Factor VIII:C Total Units | Yield % | × Purification |
|---|---|---|---|---|
| Cryoprecipitate Solution | 0.20 | 22.8 | 100 | 1 |
| Unbound | 0 | 0 | 0 | — |
| Buffer B + 0.2M NaCl Wash | 0.16 | 3.1 | 14 | 0.8 |
| Buffer B + 1M NaCl Wash | 0* | 0 | 0 | — |

*This peak initially contained approximately 25% of the Factor VIII:C activity applied to the column but it was very unstable and lost all activity after 2 h at room temperature.

c. Purification by the method of Faure et al.

3.8 g human cryoprecipitate was dissolved using a vibromixer in 11 ml Buffer C (1% sucrose, 1% human serum albumin, 0.1 M lysine, 0.1 M sodium acetate, pH 5.5) and adsorbed twice with Rehsorptar as in (a). The pH of the solution, which was 6.4 at this point, was lowered to 5.5 by slow addition of 10% acetic acid with stirring and the resultant heavy precipitate removed as in (b). 3.5 ml of clarified cryoprecipitate solution was applied to a 10 ml column of AH-Sepharose (Pharmacia) (10×0.55 cm), equilibrated in Buffer C, at a flow rate of 12 ml/h. The column was washed with Buffer C until the absorbance of the eluate was less than 0.1, with Buffer C containing 0.2 M NaCl and finally with Buffer C containing 1 M NaCl.

| Fraction | Factor VIII:C (Total Units) | Yield (%) |
|---|---|---|
| Cryoprecipitate solution | 24.7 | 100 |
| Unbound | 0 | 0 |
| Buffer C + 0.2M NaCl Wash | 3.9 | 16 |
| Buffer C + 1M NaCl Wash | 7.0 | 28 |

Neither specific activity nor level of purification is meaningful in this example due to the high concentration (10 mg/ml) of albumin present in all fractions.

EXAMPLE 2

This example demonstrates the distribution of other proteins of interest—fibronectin, von Willebrand's factor (Factor VIII:R) and fibrinogen—on purification of Factor VIII:C from human cryoprecipitate by the claimed process.

The purification procedure was as described in Example 1(a). The recoveries in each fraction shown below are expressed as a percentage of the amount of that protein applied to the resin.

| | Cryoprecipitate | Column void & Buffer A + 0.3M NaCl + 10 mM CaCl$_2$ | Buffer A + 0.4M NaCl + 10 mM CaCl$_2$ | Buffer A + 0.5M CaCl$_2$ |
|---|---|---|---|---|
| Total protein | 100 | 95 | 2 | 1 |
| Fibronectin | 100 | + | 3 | 1 |
| Fibrinogen | 100 | + | 0.5 | 0.5 |
| Factor VIII:C | 100 | 3 | 24 | 57 |
| von Willebrand's Factor | 100 | + | 23 | 3 |
| Factor VIII:C (Units/mg) | 0.18 | 0.007 | 2.0 | 9.1 |

+ not determined. However, since 96% of the applied protein was eluted from the column and fibronectin and fibrinogen are present in high concentrations in cryoprecipitate these proteins must elute largely in this fraction.

EXAMPLE 3

This example compares the fibronectin and fibrinogen contents of Factor VIII:C purified from human cryoprecipitate by the claimed process with a commercial high purity Factor VIII:C (Factorate®, Generation IIB, Armour Pharmaceutical).

The purification procedure was as described in Example 1(a).

| Fraction | Factor VIII:C (U/mg) | Fibronectin μg/U FVIII:C | Fibrinogen μg/U FVIII:C |
|---|---|---|---|
| Factorate Gen IIB | 4.2 | 4 | 146 |
| Buffer A + 0.4M NaCl + 10 mM CaCl$_2$ | 2.0 | 75 | 143 |
| Buffer A + 0.5M CaCl$_2$ | 9.1 | 11 | 36 |
| Pool of both AH- | 4.4 | 30 | 68 |

| Fraction | Factor VIII:C (U/mg) | Fibronectin μg/U FVIII:C | Fibrinogen μg/U FVIII:C |
|---|---|---|---|
| Sepharose washes | | | |

EXAMPLE 4

This example demonstrates the use of the claimed process to purify Factor VIII:C from human plasma. It also illustrates the efficacy of proteolytic inhibitors, specifically thrombin inhibitors such as hirudin, in improving the yield of Factor VIII:C in this purification.

Solid NaCl was added to human plasma to raise its conductivity to 30-35 mS/cm. In one run, the column was run without using inhibitors. In a second run, benzamidine (0.5 M) and pancreatic trypsin inhibitor (Trasylol®, 1 mg/ml) were added to final concentrations of 1 mM and 0.01 mg/ml respectively. In a third run, hirudin (Calbiochem Co., 25 U/ml) was added instead, to a final concentration of 1 Unit/ml. 5 ml of plasma was applied to a 4 ml (4×0.55 cm) column of AH-Sepharose (Pharmacia) equilibrated in Buffer A (20 mM imidazole, 0.1 M lysine, 0.02% azide, pH 6.8) containing 0.3 M NaCl at a flow rate of 12 ml/h. If proteolytic inhibitors had been added to the plasma they were also added to column running buffers. The column was washed with equilibration buffer (see Example 1) until the absorbance at 280 nm of the eluate was less than 0.02, and was then eluted with 0.5 M $CaCl_2$ in Buffer A.

| Inhibitors | Fraction | Factor VIII:C U/mg | Factor VIII:C Total Units | Factor VIII:C Yield (%) | × Purification |
|---|---|---|---|---|---|
| — | Plasma | 0.014 | 2.8 | 100 | 1 |
| None | Unbound | 0.001 | 0.2 | 9 | — |
|  | Buffer A + 0.5M $CaCl_2$ wash | 0.44 | 1.1 | 39 | 32 |
| Benzamidine + Trasylol | Unbound | 0.001 | 0.1 | 4 | — |
|  | Buffer A + 0.5M $CaCl_2$ wash | 0.67 | 2.5 | 90 | 48 |
| Hirudin | Unbound | 0.001 | 0.21 | 8 | — |
|  | Buffer A + 0.5M $CaCl_2$ wash | 0.60 | 2.0 | 72 | 43 |

It can be seen that even without inhibitors the present process effectively purifies Factor VIII:C by a factor of well over 10:1, that is, 20:1, 25:1, 30:1, or better, depending on the particular fraction that is collected. With inhibitors, the purification factor is even higher, and can exceed 40:1. At any given degree of purification the yield, i.e. the amount of Factor VIII:C fed to the process which is recovered as purified product, is higher than can be attained using prior art processes to the same degree of purification. Yields of over 30% can be achieved even without inhibitors, and yields over 50%, and as high as 70-90%, can be attained with inhibitors. This combination of purification and yield is highly advantageous and unobvious.

What is claimed is:

1. A process for purifying Factor VIII:C from source material containing antihemophilic factor, comprising
   (a) providing an aqueous solution of said source material which has a pH of 6.0 to about 8.0, and a conductivity of about 25 mS/cm to 35 mS/cm,
   (b) equilibrating aminohexyl agarose to the pH of said solution,
   (c) adsorbing antihemophilic factor from said solution onto said equilibrated aminohexyl agarose,
   (d) eluting Factor VIII:R from the aminohexyl agarose, and then
   (e) eluting the Factor VIII:C from the aminohexyl agarose.

2. The process of claim 1 wherein the pH of said source material is 6.0 to 7.5.

3. The process of claim 1 wherein the pH of said source material is 6.5 to 7.2.

4. The process of claim 1 wherein the aminohexyl agarose contains at least about 10 micromoles of aminohexyl chains per gram.

5. The process of claim 1 wherein the source material is plasma which contains AHF.

6. The process of claim 1 wherein the source material is a plasma concentrate which contains AHF.

7. The process of claim 1 wherein the source material is a cryoprecipitate which contains AHF.

8. The process of claim 1 wherein the source material also contains fibronectin, and the fibronectin is eluted with the Factor VIII:R.

9. The process of claim 1 wherein the source material also contains fibrinogen, and the fibrinogen is eluted with the Factor VIII:R.

10. The process of claim 1 wherein the Factor VIII:C is purified with a yield of at least about 30%.

11. The process of claim 1 wherein the Factor VIII:C is purified with a yield of at least about 50%, and wherein a proteolytic inhibitor is present in steps (a), (b), (c) and (d) in a small but effective amount to inhibit proteolysis of the Factor VIII:C.

12. The process of claim 1 wherein the Factor VIII:C is purified by a factor of at least about 10 times its purity in the source material.

13. The process of claim 1 wherein the Factor VIII:C is purified by a factor of at least about 20 times its purity in the source material.

14. The process of claim 1 wherein the Factor VIII:C is eluted with a buffered aqueous solution containing 1.0 M NaCl.

15. The process of claim 1 wherein the Factor VIII:C is eluted with an aqueous buffered solution containing 0.3 to 0.5 M $CaCl_2$.

16. The process for purifying Factor VIII:C from source material containing antihemophilic factor, comprising
   (a) providing an aqueous solution of said source material which has a pH of 6.0 to about 8.0 and a conductivity of about 25 mS/cm to 35 mS/cm,
   (b) equilibrating aminohexyl agarose to the pH of said solution,
   (c) adsorbing antihemophilic factor from said solution onto said equilibrated aminohexyl agarose, and then
   (d) eluting the Factor VIII:C from the aminohexyl agarose.

17. The process of claim 16 wherein the source material is plasma which contains antihemophilic factor.

18. The process of claim 16 wherein the source material is a plasma concentrate which contains antihemophilic factor.

19. The process of claim 16 wherein the source material is a cryoprecipitate which contains antihemophilic factor.

20. The process of claim 16 wherein the pH of the aqueous solution provided in step (a) is 6.0 to 7.5.

21. The process of claim 16 wherein the pH of the aqueous solution provided in step (a) is 6.5 to 7.2.

* * * * *